United States Patent [19]

Millner

[11] Patent Number: 4,955,876
[45] Date of Patent: Sep. 11, 1990

[54] BILI BOTTOM DIAPERS

[75] Inventor: Patricia M. Millner, Brainerd, Minn.

[73] Assignee: The Pennsylvania Research Corporation, University Park, Pa.

[21] Appl. No.: 138,879

[22] Filed: Feb. 29, 1988

[51] Int. Cl.$^5$ .............................................. A61F 13/16
[52] U.S. Cl. .................................. 604/385.2; 604/370
[58] Field of Search ............... 604/393, 394, 358, 370, 604/385.1, 386, 395, 397, 385.2

[56] References Cited

U.S. PATENT DOCUMENTS

| | | | |
|---|---|---|---|
| 3,488,778 | 1/1970 | Goujon et al. | 604/358 |
| 3,509,881 | 5/1970 | Sabee | 604/397 |
| 3,599,640 | 8/1971 | Larson | 604/394 |
| 3,688,767 | 9/1972 | Goldstein | 604/394 |
| 3,756,878 | 9/1973 | Willot | 604/358 |
| 4,249,532 | 2/1981 | Polansky | 604/385.1 |
| 4,430,086 | 2/1984 | Repke | 604/385.2 |
| 4,486,192 | 12/1984 | Sigl | 604/385.1 |
| 4,560,380 | 12/1985 | Tharel | 604/385.1 |
| 4,585,447 | 4/1986 | Karami | 604/385.2 |
| 4,585,450 | 4/1986 | Rosch et al. | 604/390 |
| 4,718,901 | 1/1988 | Singheimer | 604/385.2 |

FOREIGN PATENT DOCUMENTS

| | | | |
|---|---|---|---|
| 0594375 | 9/1925 | France | 604/397 |
| 2215178 | 8/1974 | France | 604/397 |
| 2499371 | 8/1982 | France | 604/358 |
| 2103930 | 3/1983 | United Kingdom | 604/358 |
| 2112268 | 7/1983 | United Kingdom | 604/358 |

Primary Examiner—Stephen C. Pellegrino
Assistant Examiner—Sharon Rose
Attorney, Agent, or Firm—Thomas J. Monahan

[57] ABSTRACT

Disclosed is a disposable diaper which is comprised of a UV light permeable material which will effectively contain excretements and maximize the surface area exposed to the phototherapeutic light.

5 Claims, 1 Drawing Sheet

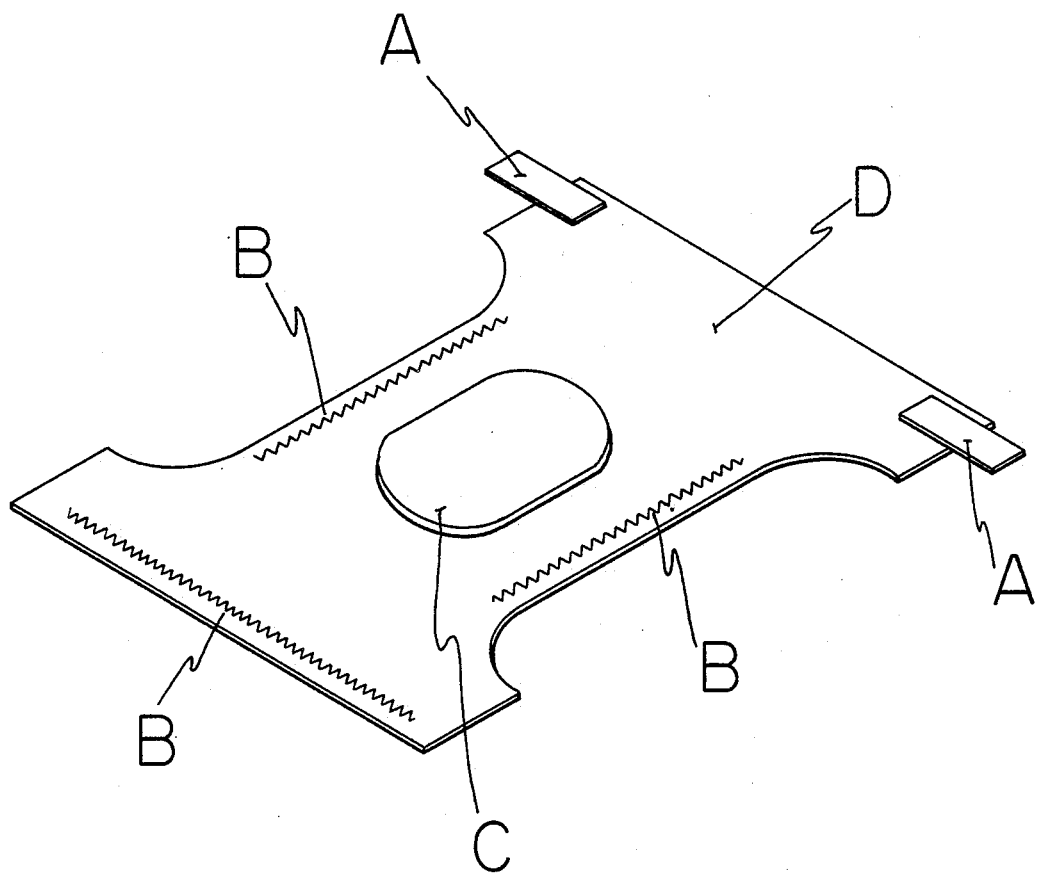
Figure I

BILI BOTTOM DIAPERS

BACKGROUND OF THE INVENTION

This invention relates to diapers capable of being used effectively for newborn infants affected with hyperbilirubinemia by increasing the skin surface area exposed to light.

DESCRIPTION OF THE PRIOR ART

Currently no diaper is available that is capable of being used effectively under phototherapy lights. Surgical masks are now being used simply because of their small size. However, they do not adequately provide the containment or the lightpermeability of the diaper of the present invention, nor do they adequately cover the bottom and contain the stool, thus resulting in increased nursing labor spent in cleaning infants and isolettes.

SUMMARY AND OBJECTS OF THE INVENTION

The object of this invention is to enable infants under phototherapy lights to break down bilirubin at a fast rate by increasing the surface area exposed.

Another object of this invention is to provide a diaper which will adequately cover the bottom and contain excrements of newborn infants affected with hyperbilirubinemia.

Another object of this invention is to increase surface area exposed to light.

Another object of this invention is to decrease nursing labor associated with caring for infants affected with hyperbilirubinemia.

Another object of this invention is to reduce the amount of time needed to clean up infants affected with hyperbilirubinemia.

Another object of this invention is to benefit hospital administrators, insurance carriers and parents by shortening the length of time required for hospitalizing infants affected with hyperbilirubinemia.

BRIEF DESCRIPTION OF THE DRAWINGS

FIG. 1 illustrates the diaper of the present invention.

DETAILED DESCRIPTION OF THE INVENTION

Hyperbilirubinemia is a condition that affects approximately 10-15% of all newborns born today. Newborns, due to immaturity of their livers or to a blood incompatibility with the mother's blood, develop yellowed skin called jaundice. These infants are placed under phototherapy lights to help break down the bilirubin in the skin. The body is then able to excrete the bilirubin through the stool, thus lowering the bilirubin level. The amount of time under the lights varies depending on how high the concentration of bilirubin is and how much surface area is exposed. Research has proven that infants placed naked under phototherapy lights break down bilirubin faster than a control group placed under phototherapy lights wearing a regular diaper. See Standards of Practice, American Academy of Pediatrics; 1986. The advantage of the present invention is that the diaper disclosed is better able to contain the excretments, which are a consistancy of thick tar or molasses due to the hyperbilirubinemia, and also increase the surface area exposed. The surgical masks being used do not adequately cover the bottom and contain the excrements requiring increased nursing labor spent in cleaning infants and isolettes. An infant under phototherapy has approximately 8-10 bowel movements a day.

Accordingly, the diaper of the present invention is a disposable phototherapy diaper made of a light permeable material D. It can be manufactured in four sizes, premature, small, medium, and large. The small size is illustrated in FIG. 1. The top and bottom width is approximately nine inches long with fastening tapes A on the backside. The length is approximately twelve inches with elastic B around the tapered leg areas to provide a formed fit. Elastic B is also placed along the front waistband to provide comfort and fit. A small absorbant pad approximately two and one half by three and one half inches will line the crotch area only in order that the exposed surface area C is maximized.

The diaper of the present invention is not designed to be an absorbent diaper. It is designed with a light-permeable material to increase surface area exposed to light and to contain bowel movements. It will be appreciated that various additional changes in the form and details of the above-described preferred embodiments may be effected by persons with ordinary skill in the art without departing from the spirit and scope of the invention. The present invention may be used in all hospital nurseries on new borns who have hyperbilirubinemia.

I claim:

1. A disposable phototherapy diaper intended primarily to maximize the surface area of a newborn infant exposed to phototherapy light to counteract a condition known as hyperbilirubinenemia comprising:

a sheet of flexible material permeable to an amount of biologically effective phototherapy light sufficient to reduce the concentration of bilirubin in the skin of the infant, which sheet of flexible material, when oriented in two planes prior to use, extends longitudinally between first and second ends, said first and second ends being relatively broad, extending, laterally, between left and right tabs, respectively, and having a laterally narrowed region intermediate said ends such that, when worn by the infant, said first end is contiguously receivable on the front of the infant, said second end is contiguously received on the back of the infant, and said narrowed region overlies the crotch of the infant, said narrow region being defined between laterally opposed edges which are tapered convergingly from said left and right tabs of said first end to said narrowed region then divergingly from said narrowed region to said left and right tabs of said second end so as to closely conform to the shape of the infant;

fastening means from joining said first and second tabs of said first end, respectively, to said first and second tabs of said second end when said diaper is worn by the infant; and a pad of absorbent material having a size strictly coextensive with the crotch of the infant to receive and hold liquid, including urine, excretions, said flexible material in the narrowed region simultaneously serving to receive and hold bowel excretions from the infant.

2. A disposable phototherapy diaper as set forth in claim 1
   wherein said fastening means includes pressure sensitive tape on said left and right tabs of said first end positioned for fastening engagement, respectively, with said first and second tabs of said second end when said diaper is worn by the infant.

3. A disposable phototherapy diaper as set forth in claim 1
    including elongated elastic means extending laterally along, but spaced from, said second end for holding the diaper snugly against the infant.

4. A disposable phototherapy diaper as set forth in claim 1
    including elongated elastic means extending longitudinally along, but spaced from, said laterally opposed edges for holding the diaper against the infant.

5. A disposable phototherapy diaper as set forth in claim 1
    wherein said first and second ends including said left and right tabs thereof and said laterally opposed edges are engaged with the skin of the infant when the diaper is worn by the infant but that said narrowed region defines a cavity between said diaper and said infant for the reception and containment of bowel excretions.

* * * * *